United States Patent [19]

Iwata et al.

[11] Patent Number: 4,884,213

[45] Date of Patent: Nov. 28, 1989

[54] METHOD FOR QUANTITATIVE ANALYSIS OF ANALYTE IN LIQUID SAMPLE USING ANALYTICAL ELEMENT

[75] Inventors: Yuzo Iwata; Hajime Makiuchi; Masao Kitajima, all of Asaka, Japan

[73] Assignee: Fuji Photo Film Co., Ltd., Kanagawa, Japan

[21] Appl. No.: 311,444

[22] Filed: Feb. 15, 1989

Related U.S. Application Data

[63] Continuation of Ser. No. 900,533, Aug. 26, 1986, abandoned.

[30] Foreign Application Priority Data

Aug. 26, 1985 [JP] Japan ................................ 60-188226

[51] Int. Cl.⁴ ...................... G01N 35/02; G01N 21/00
[52] U.S. Cl. .................................... 364/497; 364/498; 364/558; 364/571.01; 356/243; 356/431; 422/67
[58] Field of Search .................. 364/497, 498, 571.01, 364/573, 558; 356/431, 436, 243; 422/64, 65, 66, 67; 436/43, 47; 93/1 G

[56] References Cited

U.S. PATENT DOCUMENTS

| | | | |
|---|---|---|---|
| 2,554,414 | 5/1951 | McClendon | 436/44 |
| 4,338,279 | 7/1982 | Orimo et al. | 364/497 |
| 4,472,505 | 9/1984 | Manabe et al. | 364/498 |
| 4,539,296 | 9/1985 | Manabe | 436/43 |
| 4,587,624 | 5/1986 | Banno | 364/497 |
| 4,678,755 | 7/1987 | Shinohara et al. | 436/43 |
| 4,832,488 | 5/1989 | HIrai et al. | 356/402 |

Primary Examiner—Parshotam S. Lall
Assistant Examiner—Ellis B. Ramirez
Attorney, Agent, or Firm—Jules E. Goldberg

[57] ABSTRACT

In a method for quantitatively analyzing an analyte in a liquid sample by applying the liquid sample on one of a set of analytical elements and measuring a color developed in the analytical element through reflection photometory in which said set of analytical elements are the same elements as a standard element except for deviation of sensitivity to the analyte, but said deviation of sensitivity is essentially equivalent to each other among the set of analytical elements, the calibration curve of the standard element with respect to said analyte being predetermined, an improvement involving the preparation of a linear equation for defining a relationship between an optical reflection density value $OD_x$ to be measured on an analytical element belonging to said set of the analytical elements and an optical reflection density value $OD_s$ being predetermined on the standard analytical element, in which the optical reflection density values $OD_x$ and $OD_s$ are those to be determined on colors developed on the respective elements upon application of a liquid sample containing the analyte in the same content $C_x$.

7 Claims, 7 Drawing Sheets

METHOD FOR QUANTITATIVE ANALYSIS OF ANALYTE IN LIQUID SAMPLE USING ANALYTICAL ELEMENT

This is a continuation of application Ser. No. 900,533, filed Aug. 26, 1986 now abandoned.

BACKGROUND OF THE INVENTION

1. Field of the Invention

This invention relates to a method for quantitative analysis of an analyte in a liquid sample using an analytical element. More particularly, this invention relates to an improvement in a method for quantitatively analyzing an analyte in a liquid sample by applying the liquid sample on one of a set of analytical elements and measuring a color developed in the analytical element through reflection photometry in which said set of analytical elements are the same elements as a standard element except for deviation of sensitivity to the analyte, but said deviation of sensitivity is essentially equivalent to each other among the set of analytical elements, the calibration curve of the standard element with respect to said analyte being predetermined.

2. Description of prior arts

As a method for quantitative analysis of an analyte (i.e., a substance to be analyzed) in a liquid sample, there has been generally employed a reaction-in-solution system involving a homogeneous reaction in a dilute solution and a procedure of measuring a light transmitted through the solution. This system gives analytical data with high accuracy, so long as the system is conducted by a skilled operator using a long period of time.

In the field of clinical tests, however, an analytical system which can be operated more simply and more rapidly is strongly requested by people concerned, such as medical doctors.

In answer to the above-mentioned request, a dry analytical system using an analytical element in the form of a sheet containing a dry reagent responsive to the analyte has been proposed to replace the above analytical system involving the reaction in a solution. In particular, a multilayer analytical element comprising a number of laminated layers in the element has been paid attention.

In the dry analytical system, the quantitative determination of an analyte in a liquid sample is performed by applying the liquid sample of the analytical element and measuring a color developed in the element through reflection photometry. It is known that the relationship between a content of an analyte in an applied liquid sample and the optical reflection density value observed on the color development due to the application of the liquid sample does not follow Beer's law, while the relationship between a content of an analyte in a liquid sample and the transmittance value observed on the color development in a solution due to the introduction of the liquid sample does follow such law. Accordingly, in the case that the reflection photometry is employed in the analysis, a calibration curve which shows the relationship between a content of an analyte in an applied liquid sample and the optical reflection density to be observed on the color development due to the application of the liquid sample is ought to be predetermined for each kind of analytical element.

Generally, the same calibration curve is applicable to all analytical systems involving the same analyte and analytical elements belonging to the same nature, for example, those having the same composition. However, in practice the compositions of the analytical elements slightly vary depending upon the conditions of their preparations. Otherwise, even if analytical elements having the almost the same compositions are prepared, the analytical elements are apt to be denatured slighty in the course of their storage under influence of light, heat, humidity and so on. Accordingly, if a precise quantitative determination is intended, it is preferred to prepare a calibration curve on each set of the analytical elements, in which the analytical elements in one set are considered to have essentially the same composition and the same sensitivity to the analyte because these elements were prepared under the same conditions and have been stored under the same conditions. The procedure of the preparation of a calibration curve for each set of analytical elements is time-consuming and accordingly is not advantageous in the practical operation.

As is described in the above, the quantitative analysis based on the reaction-in-solution, namely wet system, follows the Beer's law. Accordingly, it is known that a calibration curve determined on a standard analytical element is well applicable with simple adjustment to an analytical element which is deviated with respect to the composition and sensitivity in the course of its preparation and/or its storage. For instance, Japanese Patent Provisional Publication No. 58(1983)-109837 teaches a method for adjusting a predetermined calibration curve which comprises a step of measuring an absorbance for at least one sample having a known concentration and a step of adjusting the calibration curve based on the measured absorbance and the absorbance corresponding to the sample having the same concentration, the latter absorbance being obtained using the predetermined calibration curve. This adjusting method is very simple but is only applicable to a measuring system based on measurement of transmitted light.

In more detail, since the measuring system utilizing transmission of light follows the Beer's law, the relationship between the concentration or content of an analyte in a sample and the optical transmission density can be expressed by a linear equation. This means that such relationship can be expressed by a straight line in a graph. Accordingly, the deviation of the sensitivity of the transmittance-measuring system can be easily adjusted by such simple method.

In contrast, such simple adjusting method is not applicable to the measuring system based on reflection photometry, because the relationship between the concentration or content of an analyte in a sample and the optical reflection density is expressed not by a linear equation but by a very complicated equation. This means that such relationship can be expressed not by a straight line but by a curve in a graph. An example of such curve is illustrated in the attached. FIG. 1. In FIG. 1, a calibration curve for a standard analytical element for glucose analysis in the form of an integral multilayer element which indicates a relationship between a glucose content in serum and an optical reflection density value is illustrated by the solid curve. The dotted curve in FIG. 1 shows a calibration curve for an analytical element which is deviated in the sensitivity to glucose from the standard element. As is understood from the curves, it is very difficult to determine the relationship between the calibration curve for the standard analytical element and the calibration curve for the deviated analytical element. Accordingly, the deviation of the sensitivity of the measuring system based on reflection photometry cannot be adjusted by the above-mentioned simple method disclosed in the prior art.

As to the relationship between the transmittance and reflectance in photographic color prints, F. C. Williams and F. R. Clapper have proposed in Journal of the Optical Society of America, Vol. 43, No. 7, 595–599- (July, 1953) a conversion equation, but the proposed conversion equation is extremely complicated using a number of parameters. Accordingly, it is not easy to utilize the proposed conversion equation in analytical systems to be performed in practice.

SUMMARY OF THE INVENTION

The present inventors have studied reflection photometry with respect to quantitative analysis using analytical elements and discovered that there is a linear relationship between an optical reflection density on a color developed upon application of a liquid sample on a standard analytical element and an optical reflection density on a color developed upon application of the same liquid sample on a deviated analytical element. The term "deviated analytical element" means an analytical element having essentially the same composition as the standard analytical element but having a sensitivity to an analyte to be detected which is different from the corresponding sensitivity of the standard analytical element. Such difference in the sensitivity is generally caused by variation or fluctuation of the conditions of the preparation of analytical elements or denaturation of the analytical element in the course of their storage under influence of light, heat, humidity and so on.

Accordingly, it is an object of the present invention to provide a method for quantitative analysis of an analyte in a liquid sample using an analytical element which is slightly deviated in its sensitivity to the analyte from a standard analytical element.

It is another object of the invention to provide a simple method for performing quantitative analysis of an analyte in a liquid sample using an analytical element which is slightly deviated in its sensitivity to the analyte from a standard analytical element.

There is provided by the present invention an improvement in a method for quantitatively analyzing an analyte in a liquid sample by applying the liquid sample on one of a set of analytical elements and measuring a color developed in the analytical elements through reflection photometory in which said set of analytical elements are the same elements as a standard element except for deviation of sensitivity to the analyte, but said deviation of sensitivity is essentially equivalent to each other among the set of analytical elements, the calibration curve of the standard element with respect to said analyte being predetermined, the improvement comprising the steps of:

(I) applying two standard solutions containing the analyte in contents $C_1$ and $C_2$ different from each other on two analytical elements, respectively, these analytical elements being selected from said set of analytical elements, and measuring colors developed on the elements through reflection photometry to obtain optical reflection density values $OD_1$ and $OD_2$, respectively;

(II) preparing a linear equation for defining a relationship between an optical reflection density value $OD_x$ to be measured on an analytical element belonging to said set of the analytical elements and an optical reflection density value $OD_s$ being predetermined on the standard analytical element, in which the optical reflection density values $OD_x$ and $OD_s$ are those to be determined on colors developed on the respective elements upon application of a liquid sample containing the analyte in the same content $C_x$, the preparation being made utilizing the calibration curve and the optical reflection density values $OD_{x}1$ and $OD_{x}2$ obtained in the step (I);

(III) applying a liquid sample containing the analyte in a unknown amount on an analytical element belonging to said set of analytical elements, and measuring a color developed on said element through reflection photometry to obtain an optical reflection density value; and (IV) determining the content of the analyte in the applied liquid sample according to the above-prepared linear equation and the predetermined calibration curve.

DETAILED DESCRIPTION OF THE INVENTION

Figure 1:
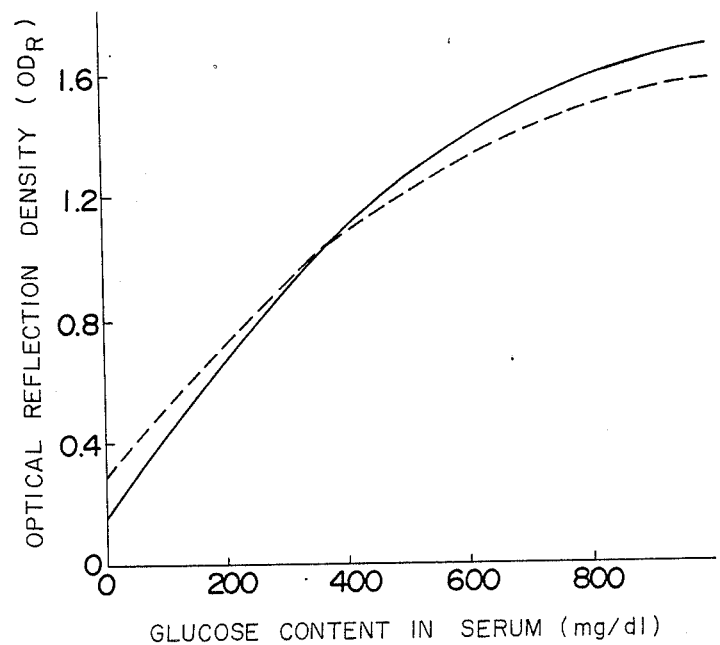
FIG. 1 shows calibration curves for a relationship between glucose content in serum and optical reflection density measured on color developed in an analytical element having received the serum sample.

The analytical method of the present invention comprises the aforementioned four steps. Each step is described in more detail below.

The first step (I) and the second step (II) are steps for determining the relationship between the sensitivity of the standard analytical element and the sensitivity of the analytical elements to be calibrated.

The first step comprises applying two standard solutions containing the analyte in contents $C_1$ and $C_2$ different from each other on two analytical elements, respectively, these analytical elements being selected from said set of analytical elements and measuring colors developed on the elements through reflection photometry to obtain optical reflection density values $OD_{x1}$ and $OD_{x2}$, respectively.

There is no specific limitation with respect to the analytical element to be employed in the method of the present invention, so long as the element is subjected to relfection photometry. For instance, there can be mentioned multilayer analytical elements supplied by Eastman Kodak under the tradename of Ektachem and multilayer analytical elements by Fuji Photo Film Co., Ltd. under the tradename of Drychem.

There is also no specific limitation with respect to the analyte to be detected by the use of the method of the present invention. For instance, the method of the invention can be utilized to quantitatively determine glucose content, total protein content, urea-nitrogen (BUN) content, bilirubin content, contents of other substances, amylase activity, alkaline phosphotase activity, and activities of other enzymes in a liquid sample such as whole blood, serum, plasma, saliva, urine, or the like.

In the first step, two analytical elements are taken out of set of analytical elements. All of the analytical elements belonging to the above-mentioned set are considered to have the equivalent composition and the equivalent sensitivity to an analyte to be analyzed to each other. Accordingly, any two elements can be selected from the set of the analytical elements. Alternatively, three analytical elements can be employed. In this case, the third analytical element is employed for obtaining an average value in combination with the first or second element. In the same way, more than three analytical elements can be employed in this stage.

The standard solutions employed in this stage contain different amounts of the same analyte (contents are identified by $C_1$ and $C_2$, respectively) as the analyte of the analytical system under consideration. The composition of the standard solution other than the analyte can be the same as or different from the composition of the liquid sample to be analyzed, so long as the content of the analyte in the standard solution is known. For example, in the case the liquid sample to be analyzed is a whole blood or serum, the standard solution can be a serum containing a known amount of the analyte or a commercially available standard solution such as those supplied under tradenames of Monitrol and Versatol. The standard solution preferably is the equivalent or as similar as possible in the physical characteristics such as viscosity to the liquid sample to be analyzed.

The color developed on both elements are then measured through reflection photometry to obtain optical reflection density values $OD_1$ and $OD_2$, respectively.

The second step comprises preparing a linear equation for defining a relationship between an optical reflection density value $OD_x$ to be measured on an analytical element belonging to the above-mentioned set of the analytical elements and an optical reflection density value $OD_s$ being predetermined on the standard analytical element. The optical reflection density values $OD_x$ and $OD_s$ are those to be determined on colors developed on the respective elements upon application of a liquid sample containing the analyte in the same content $C_x$. The preparation of the linear equation is made utilizing the calibration curve on the standard analytical element and the optical reflection density values $OD_{x1}$ and $OD_{x2}$ obtained in the step (I).

The linear equation can be given in the form of:

$$OD_x = A \cdot OD_s + B$$

in which A and B are constant values obtained from the equations:

$$OD_{x1} = A \cdot OX_{s1} + B$$

$$OD_{x2} = A \cdot OX_{s2} + B$$

in which $OX_{x1}$ is as defined above and $OX_{s1}$ is an optical reflection density value to be determined on the standard analytical element upon application of a liquid sample containing the analyte in the content $C_{x1}$, and $OX_{x2}$ is as defined above and $OX_{s2}$ is an optical reflection density value to be determined on the standard analytical element upon application of a liquid sample containing the analyte in the content $C_{x2}$.

In the second step, the linear equation is given by the functional equation as above or expressed graphically.

In the practical analytical procedure, the above-mentioned linear equation is preferably stored either in the form of the functional equation or a graph in a memory of a computer for determining the desired results precisely within a short time of period.

The third step and the fourth step are steps for actually analyzing a liquid sample containing a unknown amount of the analyte using the deviated analytical element.

The third step comprises applying a liquid sample containing the analyte in a unknown amount on an analytical element belonging to the above-mentioned set of deviated analytical elements and measuring a color developed on said element through reflection photometry to obtain an optical reflection density value.

The measurement of the color developed on the element through reflection photometry can be done in the known way.

The fourth step comprises determining the content of the analyte in the applied liquid sample according to the above-prepared linear equation and the predetermined calibration curve.

The determination of the content of the analyte in the applied liquid sample is done based on the linear equation prepared in the step (II) and the calibration curve predetermined on the standard analytical element. In this determination, the optical reflection density value measured on the deviated analytical element is in the first place converted into an optical reflection density value of the standard analytical element, in which the latter value is positively or negatively deviated from the former value. The latter optical reflection density value obtained upon the conversion is then converted into a content of the analyte in the applied liquid sample according to the calibration curve previously determined on the standard analytical element.

Figure 2:
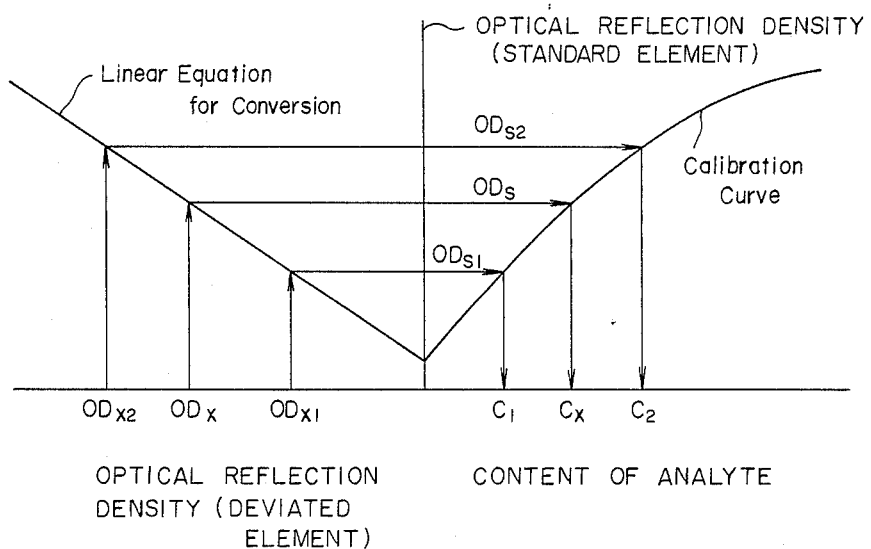
FIG. 2 illustrates the procedure of conversion of an optical reflection density observed on a deviated analytical element into the content of the analyte in the applied liquid sample for quantitative analysis.

The above conversion procedures are described in more detail by referring to FIG. 2.

In FIG. 2, the axis of abscissa on the left side indicates an optical reflection density measured on a deviated analytical element and the axis of abscissa on the right side indicates a content of the analyte in a liquid sample. The axis of ordinate indicates an optical reflection density to be measured on the standard analytical element. The curved line on the right side is the calibration curve prepared on the standard analytical element, and the straight line on the left side is the line representing the linear equation prepared in the second step.

In FIG. 2, the relationships among the optical reflection density values $OD_{x1}$ and $OD_{x2}$ measured on the deviated analytical elements, the optical reflection density vlaues $OD_{s1}$ and $OD_{s2}$ obtained respectively upon the above-mentioned conversion, and the contents of the analyte $C_{x1}$ and $C_{x2}$ in the applied liquid samples are clear.

Thus, the conversion from the optical reflection density value $OD_x$ measured on the deviated analytical element to other content of the analyte $C_x$ in the applied liquid sample is easily made actually or imaginarily via the optical reflection density value $OD_s$.

The present invention is further described by the following examples.

EXAMPLE 1

A set of slides for glucose analysis each containing an integral multilayer analytical element for quantitative analysis of glucose were prepared according to the Example 1 described in Japanese Patent Provisional Publication No. 59(1984)-20853. A half of the set of the slides were stored for 24 hours at 30° C. and 70% RH to denature the analytical elements.

The optical reflection density values of the original slide and the denatured slide were measured with no application of sample. The original slide gave an optical reflection density of 0.221, while the denatured slide gave an optical reflection density of 0.250.

Four liquid samples containing glucose in different amounts within 50 to 600 mg/dl were spotted on each of the original slide and the denatured slide, and the optical reflection density values were measured after the slides were incubated.

Figure 3:
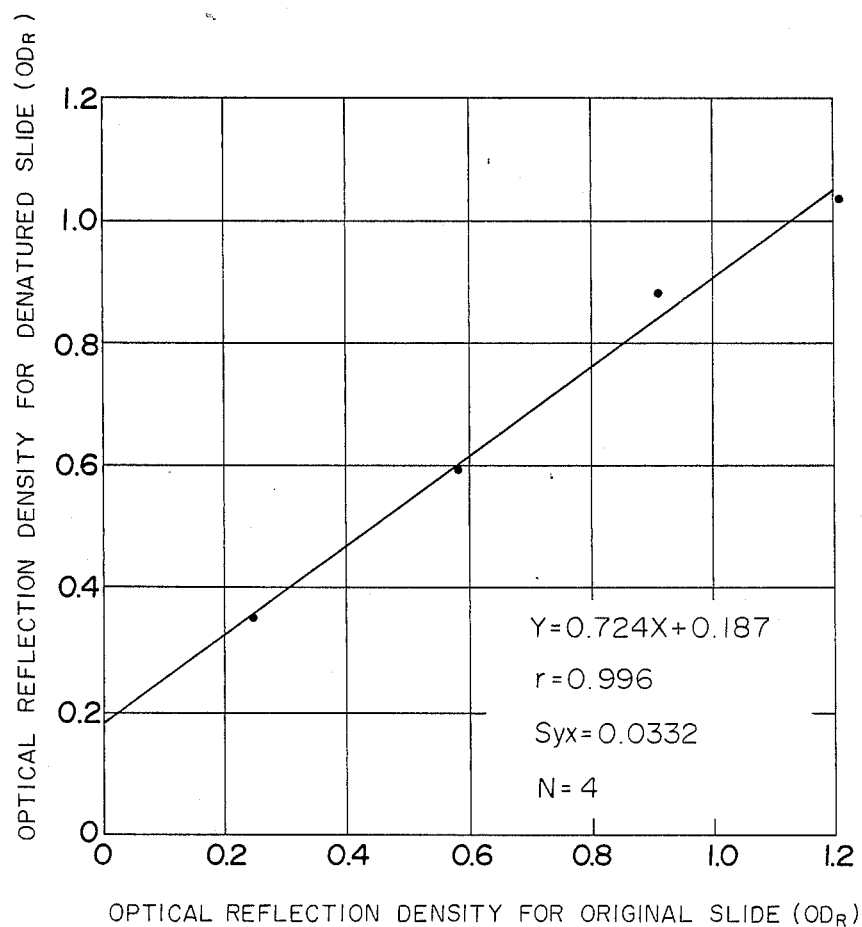
FIG. 3 illustrates a relationship for an analytical element for glucose analysis between an optical reflection density for an original slide and an optical reflection density for a denatured slide.

The results are illustrated in FIG. 3, wherein the axis of abscissa indicates an optical reflection density for the original slide and the axis of ordinate indicates an optical reflection density for the denatured slide.

FIG. 3 clearly indicates that the relationship between the optical reflection density (X) for the original slide and the optical reflection density (Y) for the denatured slide is expresed by the straight line according to the following linear equation:

$Y = 0.724X + 0.187$ $r = 0.996$ $N = 4.$

Four liquid samples each containing an unknown amount of glucose were spotted on the four denatured slides, and the optical reflection density values were measured after the slides were incubated. The measured optical reflection density values were converted into the optical reflection density values for the original slide in accordance with the above-mentioned linear equation, and then converted into the glucose content in accordance with a calibration curve previously determined using the original slide and standard liquid samples each containing a known amount of glucose. The results are set forth in Table 1 in the column (1). The values set forth in Table 1 in the column (2) are glucose content values obtained directly by calculation from the observed optical reflection density values in the manner applicable to the measuring system based on the measurement of transmitted light. The values set forth in Table 1 in the column (3) are glucose content values determined according to a standard solution system, namely, Hexokinase method.

TABLE 1

| Sample | Determined Glucose Content | | |
|---|---|---|---|
| No. | (1) | (2) | (3) |
| 1 | 69 | 65 | 70 |
| 2 | 190 | 177 | 190 |
| 3 | 308 | 283 | 301 |
| 4 | 400 | 375 | 399 |

The results in Table 1 evidently indicate that the glucose content (1) determined according to the method of the present invention is in satisfactory agreement with the values (3) determined according to the standard Hexokinase method.

EXAMPLE 2

Two sets (Lot No. 1 and Lot No. 2) of the same slides for glucose analysis were prepared separately from each other in the same manner as in Example 1.

Five liquid samples containing glucose in different amounts were spotted on each set of the slides, and the optical reflection density values were measured after the slides were incubated.

Figure 4:
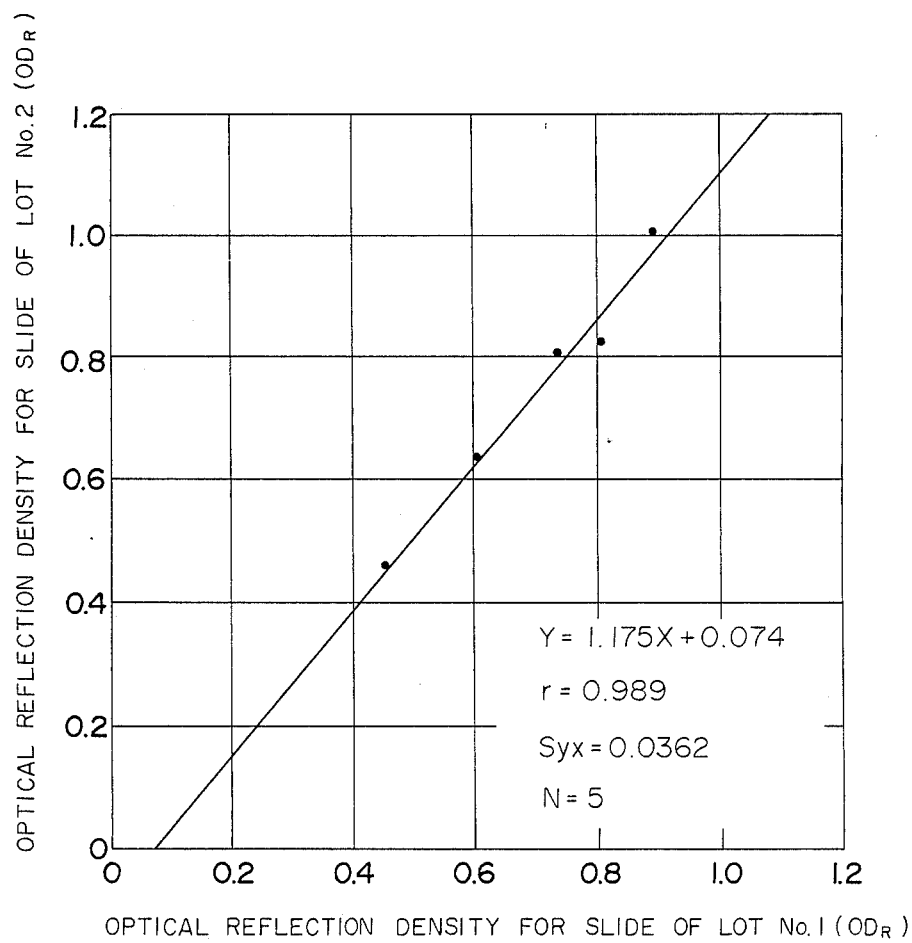
FIG. 4 illustrates a relationship for an analytical element for glucose analysis between an optical reflection density values for elements belonging to different lots.

The results are illustrated in FIG. 4, wherein the axis of abscissa indicates an optical reflection density for the slide of Lot No. 1 and the axis of ordinate indicates an optical reflection density for the slide of Lot No. 2.

FIG. 4 clearly indicates that the relationship between the optical reflection density (X) for the slide of Lot No. 1 and the optical reflection density (Y) for the slide of Lot No. 2 is expressed by the straight line according to the following linear equation:

$Y = 1.175X - 0.074$ $r = 0.989$ $N = 5.$

Four liquid samples each containing an unknown amount of glucose were spotted on the four slides of Lot No. 2, and the optical reflection density values were measured after the slides were incubated. The measured optical reflection density values were converted into the optical reflection density values for the slide of Lot No. 1 in accordance with the above-mentioned linear equation, and then converted into the glucose content in accordance with a calibration curve previously determined using the slide of Lot No. 1 and standard liquid samples each containing a known amount of glucose. The results are set forth in Table 2 in the column (4). The values set forth in Table 2 in the column (5) are glucose content values obtained directly by calculation from the observed optical reflection density values in the manner applicable to the measuring system based on the measurement of transmitted light. The values set forth in Table 2 in the column (6) are glucoe content values determined according to the standard Hexokinase method.

TABLE 2

| Sample | Determined Glucose Content | | |
|---|---|---|---|
| No. | (4) | (5) | (6) |
| 5 | 60 | 51 | 60 |
| 6 | 174 | 155 | 174 |
| 7 | 283 | 258 | 283 |
| 8 | 370 | 338 | 367 |

The results in Table 2 evidently indicate that the glucose content (4) determined according to the method of the present invention is in satisfactory agreement with the values (6) determined according to the standard Hexokinase method.

EXAMPLE 3

On a transparent colorless polyethylene terephthalate (PET) film (thickness: 180 μm) having a nitrocellulose subbing layer was coated a coating solution of the following composition to form a dry reagent layer of 40 μm thick.

| Composition of Coating Solution for Preparation of Reagent Layer | |
| --- | --- |
| Water | 600 g. |
| Sodium polyoxyethylene lauryl ethersulfate (50% aqueous solution) | 40 g. |
| Tartaric acid | 100 g. |
| Copper sulfate .5 hydrates | 150 g. |
| Sodium tartarate | 15 g. |
| LiOH.H$_2$O | 200 g. |
| Acrylamide-vinylpyrrolidone (1:1) copolymer (20% aqueous solution) | 2,000 g. |

The reagent layer was wetted with water, and on the wetted layer was placed under pressure a tricot-knitted cloth (thickness: 200 μm) of polyethylene terephthalate spun yarn (thickness corresponding to 100 S) to form a spreading layer. Thus, an integral multilayer analytical element for quantitative analysis of total protein was prepared.

The integral multilayer analytical element was cut to give a square tip (15 mm×15 mm) and encased in a plastic mount disclosed in Japanese Patent Provisional Publication No. 57(1981)-63452 to prepare an analytical slide for quantitative analysis of total protein.

Two sets of slides were further prepared in the above-stated manner; one set (Slide B) was allowed to stand for 7 days at 25° C. and 50% RH, and another set (Slide C) was allowed to stand for 14 days at 25° C. and 70% RH.

10 μl of human serum containing different amounts of total protein were separately spotted on the above Slides B and C, as well as on the original slide (Slide A). The spotted slides were incubated at 37° C. for 6 min. Subsequently, the optical reflection density on the element was measured using a light having a central wavelength of 540 nm. The measured values are set forth in Table 3.

TABLE 3

| Slide A | Slide B | Slide C |
| --- | --- | --- |
| *0.545 | 0.525 | 0.503 |
| 0.857 | 0.823 | 0.745 |
| 1.041 | 0.980 | 0.877 |
| 1.169 | 1.093 | 0.961 |

In Table 3. the values on the line with the asterisk * mean the optical reflection density values (fog values) before receiving the spotting of the sample.

Figure 5:
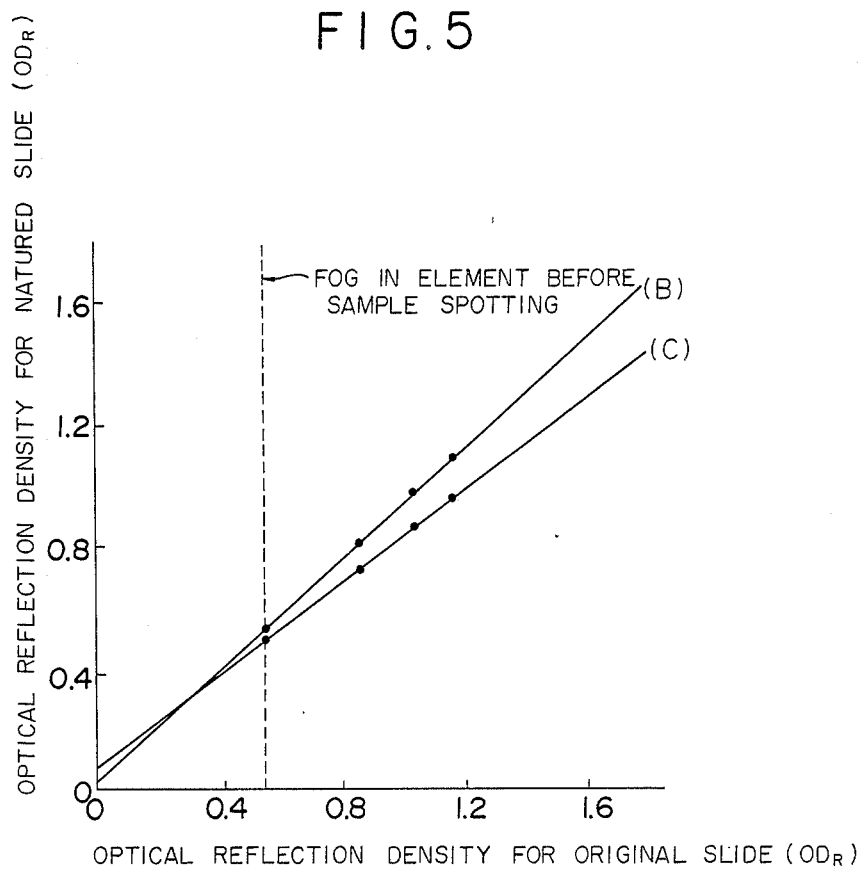
FIG. 5 illustrates relationships for an analytical element for BUN analysis between an optical reflection density for an original element and an optical reflection density for denatured elements.

The results set forth in Table 3 are illustrated in FIG. 5, wherein the axis of abscissa indicates an optical reflection density for the original slide (Slide A) and the axis of ordinate indicates an optical reflection density for the denatured slides (Slides B and C).

FIG. 5 clearly indicates that the relationship between the optical reflection density (X) for the original slide and the optical reflection density (Y) for the denatured slide is also expressed by a straight line in the case of an integral multilayer analytical element for quantitative analysis of total protein.

EXAMPLE 4

On a transparent colorless polyethylene terephthalate (PET) film (thickness: 180 μm) was coated a coating solution of the following composition to form a dry indicator layer of 10 μm thick.

| Composition of Coating Solution for Preparation of Indicator Layer | |
| --- | --- |
| Bromocresol Green | 240 mg. |
| Aqueous latex of vinyl acetate-acrylic ester copolymer (solid content: approx. 50%, pH 4.4, prepared by Daicel Corp.) | 20 g. |
| 3,3-Dimethylglutaric acid | 80 mg. |
| Water | 8 ml. |

On the dry indicator layer having a sticky surface thereon was placed under pressure the following water-repellent membrane filter to form a liquid-blocking layer.

PREPARATION OF WATER-REPELLENT MEMBRANE FILTER

A membrane filter of cellulose diacetate having thickness of 140 μm (mininum pore size: 3.0 μm, void ratio: 75%) was immersed in a solution of silicone resin in hexane and dried.

On the liquid-blocking layer were coated successively the following coating solutions to form a urease-containing reagent layer, a light-blocking layer and an adhesive layer.

| Coating Solution for Preparation of Urease-Containing Reagent Layer | |
| --- | --- |
| Gelatin | 10 g. |
| Water | 100 ml. |
| p-Nonylphenyoxypolyglycidol | 0.30 g. |
| Urease | 0.8 g. |
| Ethylenediaminetetra acetate tetrasodium salt | 0.4 g. |

The above coating solution was adjusted to pH 8 by addition of disodium orthophosphate and sodium hydroxide.

| Coating Solution for Preparation of Light-Blocking Layer | |
| --- | --- |
| TiO$_2$ fine powder | 4 g. |
| Gelatin | 4 g. |
| p-Nonylphenoxypolyglycidol | 0.15 g. |
| Water | 40 ml. |
| Coating Solution for Preparation of Adhesive Layer | |
| Gelatin | 2.5 g. |
| Water | 50 ml. |
| p-Nonylphenoxypolyglycidol | 0.15 g. |

The adhesive layer was swollen with water, and on the swollen layer was placed under pressure a cotton broadcloth (thickness: approx. 150 μm, cotton broadcloth #100) to form a spreading layer. Thus, an integral multilayer analytical element for quantitative analysis of ureanitrogen (BUN) was prepared.

The integral multilayer analytical element was cut to give a square tip and encased in a plastic mount to prepare an analytical slide for quantitative analysis of BUN.

Three sets of slides were further prepared in the above-stated manner: the first set (Slide E), the second set(Slide F) and the third set(Slide G) were allowed to stand for 3 days, 5 days and 10 days, respectively, at 25° C. and 70% RH.

Human serums containing different amounts of urea were separately spotted on the above Slides E, F and G, as well as on the original slide (Slide D). The spotted slides were incubated, and the optical reflection density on the element was measured. The measured values are set forth in Table 4.

TABLE 4

| Slide D | Slide E | Slide F | Slide G |
|---------|---------|---------|---------|
| *0.53   | 0.49    | 0.46    | 0.42    |
| 0.65    | 0.60    | 0.56    | 0.51    |
| 0.76    | 0.70    | 0.64    | 0.58    |
| 0.86    | 0.78    | 0.71    | 0.64    |
| 0.97    | 0.84    | 0.80    | 0.71    |
| 1.05    | 0.94    | 0.85    | 0.79    |

In Table 4, the values on the line with the asterisk * mean the optical reflection density values (fog values) before receiving the spotting of the sample.

Figure 6:
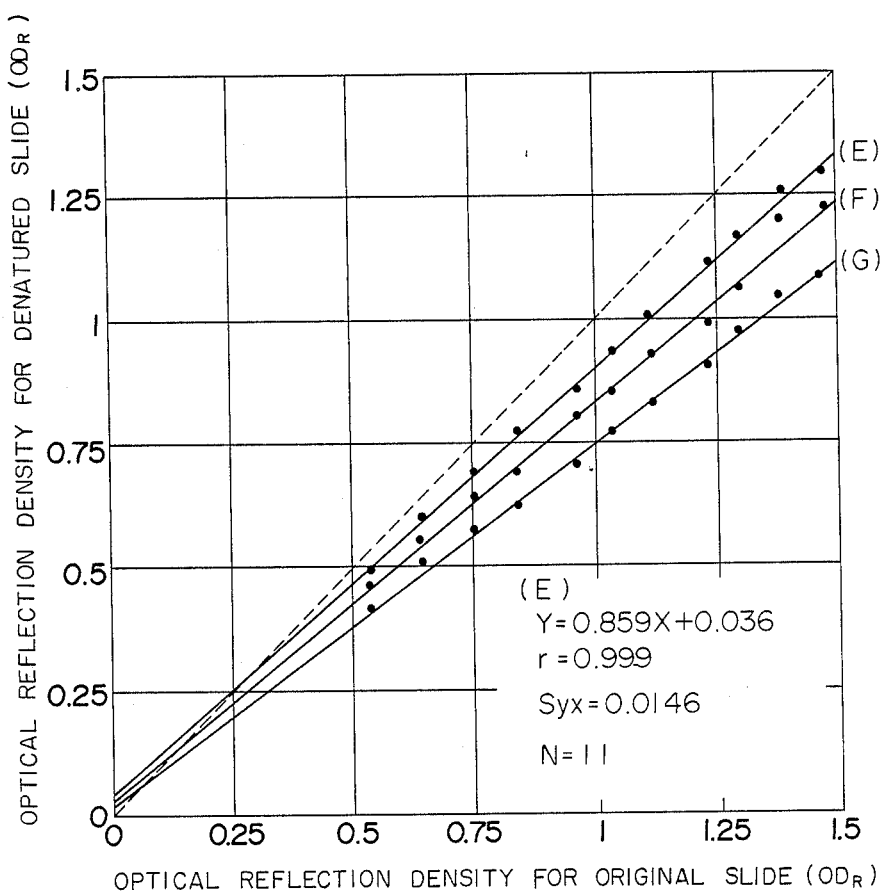
FIG. 6 illustrates other relationships for an analytical element for BUN analysis between an optical reflection density for an original element and an optical reflection density for denatured elements.

The results set forth in Table 4 are illustrated in FIG. 6, wherein the axis of abscissa indicates an optical reflection density for the original slide (Slide D) and the axis of ordinate indicates an optical reflection density for the denatured slides (Slides E, F and G).

FIG. 6 clearly indicates that the relationship between the optical reflection density (X) for the original slide and the optical reflection density (Y) for the denatured slide is also expressed by a straight line in the case of an integral multilayer analytical element for quantitative analysis of BUN.

EXAMPLE 5

Two sets (Lot No. 1 and Lot No. 2) of the same slides for BUN analysis were prepared separately from each other in the same manner as in Example 4.

Human serums containing different amounts of urea were separately spotted on the above slides. The spotted slides were incubated, and the optical reflection density on the element was measured.

Figure 7:
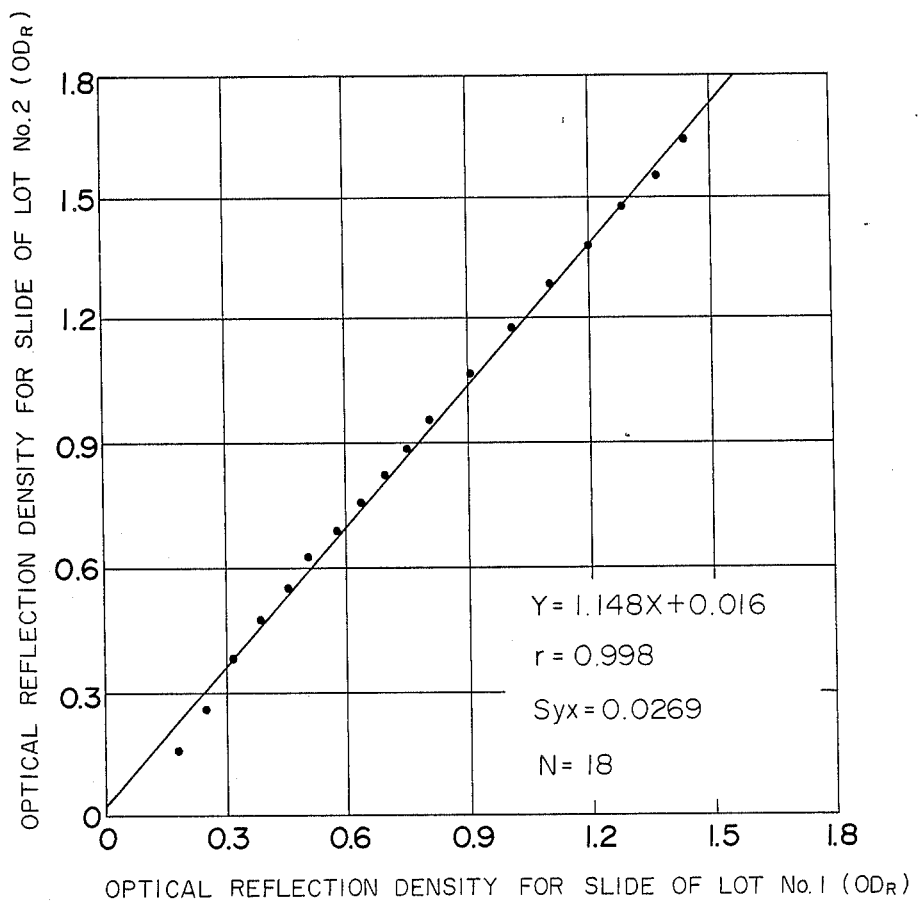
FIG. 7 illustrates a relationship for an analytical element for BUN analysis between an optical reflection density values for elements belonging to different lots.

The results are illustrated in FIG. 7, wherein the axis of abscissa indicates an optical reflection density for the slide of Lot No. 1 and the axis of ordinate indicates an optical reflection density for the slide of Lot. No. 2.

FIG. 7 clearly indicates that the relationship between the optical reflection density values for the slides belonging to different lots is also expressed by a straight line in the case of an integral multilayer analytical element for quantitative analysis of BUN.

We claim:

1. In a method for quantitatively analyzing an analyte in a liquid sample by applying the liquid sample on one of a set of analytical elements and measuring a color developed in the analytical element through reflection photometry in which said set of analytical elements are the same elements as a standard element except for deviation of sensitivity to the analyte, but said deviation of sensitivity is essentially equivalent to each other among the set of analytical elements, a calibration curve of the standard element with respect to said analyte being predetermined, the improvement comprising the steps of:

(I) applying two standard solutions containing the analyte in contents $C_1$ and $C_2$ different from each other on two analytical elements, respectively, these analytical elements being selected from said set of analytical elements, and measuring colors developed on the elements through reflection photometry to obtain optical reflection density values $OD_{x1}$ and $OD_{x2}$, respectively;

(II) preparing a linear equation for defining a relationship between an optical reflection density value $OD_x$ to be measured on an analytical element belonging to said set of the analytical elements and an optical reflection density value $OD_s$ being predetermined on the standard analytical element, in which the optical reflection density values $OD_x$ and $OD_s$ are those to be determined on colors developed on the respective elements upon application of a liquid sample containing the analyte in the same content $C_x$, the preparation being made utilizing the calibration curve and the optical reflection density values $OD_{x1}$ and $OD_{x2}$ obtained in step (I);

(III) applying a liquid sample containing the analyte in an unknown amount on an analytical element belonging to said set of analytical elements, and measuring a color developed on said element through reflection photometry to obtain an optical reflection density values; and (IV) determining the content of the analyte in the applied liquid sample according to the above-prepared linear equation and the predetermined calibration curve; wherein said linear equation is $$OD_x = A \cdot OD_s + B$$

in which A and B are constant values obtained from the equations:

$$OD_{x1} = A \cdot OD_{s1} + B$$

$$OD_{x2} = A \cdot OD_{x2} + B$$

in which $OD_{s1}$ is an optical reflection density value to be determined on the standard analytical element upon application of a liquid sample containing the analyte in the content $C_{x1}$, and $OD_{s2}$ is an optical reflection density value to be determined on the standard analytical element upon application of a liquid sample containing the analyte in the content $C_{x2}$.

2. The method of claim 1 wherein said analytical element having the deviated sensitivity to the analyte has a calibration curve crossing the calibration curve of the standard element.

3. The method as claimed in claim 1, wherein said linear equation is given graphically.

4. The method as claimed in claim 1, wherein said linear equation is stored in a memory of a computer.

5. The method as claimed in claim 1, wherein said step (II) is conducted in a computer.

6. The method as claimed in claim 1, wherein said step (IV) is conducted in a computer.

7. The method as claimed in claim 1, wherein said steps (II) and (IV) are conducted in a computer.

* * * * *